United States Patent
Stonefield

(10) Patent No.: US 8,351,666 B2
(45) Date of Patent: Jan. 8, 2013

(54) PORTABLE IMAGING SYSTEM HAVING A SEAMLESS FORM FACTOR

(75) Inventor: Andrew David Stonefield, Whitefish Bay, WI (US)

(73) Assignee: General Electric Company, Schenectady, NY (US)

( * ) Notice: Subject to any disclaimer, the term of this patent is extended or adjusted under 35 U.S.C. 154(b) by 1452 days.

(21) Appl. No.: 11/940,501

(22) Filed: Nov. 15, 2007

(65) Prior Publication Data

US 2009/0129640 A1    May 21, 2009

(51) Int. Cl.
*G06K 9/001* (2006.01)
(52) U.S. Cl. .......................... 382/128; 600/459; 206/320
(58) Field of Classification Search ................ 382/128
See application file for complete search history.

(56) References Cited

U.S. PATENT DOCUMENTS

| | | | |
|---|---|---|---|
| 4,320,147 A * | 3/1982 | Schaeufele | 514/643 |
| 5,315,999 A | 5/1994 | Kinicki et al. | |
| 5,576,284 A * | 11/1996 | van Buskirk et al. | 510/384 |
| 5,797,397 A | 8/1998 | Rosenberg | |
| 6,082,535 A * | 7/2000 | Mitchell | 206/320 |
| 6,575,596 B2 * | 6/2003 | Butt | 362/259 |
| 6,727,930 B2 * | 4/2004 | Currans et al. | 715/864 |
| 6,817,470 B1 * | 11/2004 | Goldberg | 206/320 |
| 7,290,654 B2 * | 11/2007 | Hodges | 206/320 |
| 7,724,532 B2 * | 5/2010 | Zadesky et al. | 361/752 |
| 2005/0124890 A1 * | 6/2005 | Halmann et al. | 600/446 |
| 2007/0162858 A1 | 7/2007 | Hurley et al. | |
| 2008/0267467 A1 * | 10/2008 | Sokulin et al. | 382/128 |
| 2008/0295932 A1 * | 12/2008 | Havens et al. | 150/154 |

OTHER PUBLICATIONS

"SonoSite S-Fast", retreived from the internet URL: Sonosite::S-Series::S-Fast::Overview (http://www.sonositesseries.com/s-series/s-fast/overview).

"SonoSite Launches Radically New Emergency Medicine Tool for Point-of-Care Visualization" retreived from the internet URL: Sonosite, The World Leader in Hand-Carried Ultrasound—Sonosite Launches Radically New Emergency Medicine Tool for Point-of-Care Visualization (http://www.sonosite.com/Press-Releases/news-2007-10-08.html.).

* cited by examiner

*Primary Examiner* — Phillip A Johnston
(74) *Attorney, Agent, or Firm* — The Small Patent Law Group; Dean D. Small

(57) ABSTRACT

A portable imaging system is presented. The system includes at least a display panel. Further, the system includes a control panel, where the display panel and the control panel include a seamless form factor of a single unit box, and where the seamless form factor is configured to aid in cleaning the system.

30 Claims, 7 Drawing Sheets

PORTABLE IMAGING SYSTEM HAVING A SEAMLESS FORM FACTOR

BACKGROUND

This disclosure relates generally to diagnostic imaging methods and apparatus, and more particularly, to a design of a diagnostic imaging apparatus.

Diagnostic imaging has emerged into an essential aspect of patient care. Medical images that are obtained during a diagnostic imaging session have evolved as tools that allow a clinician non-invasive means to view anatomical cross-sections of internal organs, tissues, bones and other anatomical regions of a patient. More particularly, the medical images serve the clinician in diagnosis of disease states, determination of suitable treatment options and/or monitoring the effects of treatment, to name a few. As will be appreciated, medical images may be obtained from a broad spectrum of imaging modalities, such as, but not limited to computed tomography (CT) imaging, ultrasound imaging, magnetic resonance (MR) imaging, digital mammography, X-ray imaging, nuclear medicine imaging, or positron emission tomography (PET) imaging.

Ultrasound imaging (also referred to as ultrasound scanning or sonography) is a relatively inexpensive and radiation-free imaging modality. As will be appreciated, ultrasound typically involves non-invasive imaging and is being increasingly used in the diagnosis of a number of organs and conditions, without X-ray radiation. Further, modern obstetric medicine for guiding pregnancy and childbirth is known to rely heavily on ultrasound to provide detailed images of the fetus and the uterus. In addition, ultrasound is also extensively used for evaluating the kidneys, liver, pancreas, heart, and blood vessels of the neck and abdomen. More recently, ultrasound imaging and ultrasound angiography are finding a greater role in the detection, diagnosis and treatment of heart disease, heart attack, acute stroke and vascular disease which may lead to stroke. Also, ultrasound is also being used more and more to image the breasts and to guide biopsy of breast cancer.

Further, diagnostic imaging systems, such as ultrasound imaging systems typically entail use of a user interface to control scanning operation and a display screen to view images being scanned. Typically, these imaging systems include a separate console and display screen. However, as will be appreciated, some imaging systems may include a box or tablet shaped scanner, with buttons disposed adjacent to the display screen. In either embodiment, the display and the console are generally physically separate components that may be joined together to form the imaging system.

In the case of an ultrasound imaging system, a display screen is used to view images produced by an image acquisition device, such as a probe. Recently, the ultrasound imaging system has been known to include a screen that is often a flat panel framed in plastic without any other protection against chemicals or fluid splatter. Furthermore, in the imaging systems using multiple components there are part lines or seams where the components are joined together, further increasing the risk of contamination by infectious diseases and/or bacteria in a medical environment in which a diagnostic imaging system may be employed. A similar risk of contamination is posed around keypads, mechanical buttons, trackballs, and touch pads that are part of the diagnostic imaging system.

Cleaning the seams between all the components is an onerous task that may have to be performed daily by a clinician in meticulous detail. However, there is a risk that the diagnostic imaging system may not be totally cleaned because small splatters of blood and other bodily fluids may go unseen. To ameliorate this problem, flexible plastic films or sheets that may be layered onto consoles and keyboards have been used. Unfortunately, these drapes or covers tend to interfere with the visibility of images and the operation of the imaging systems and may not always be completely effective in eliminating contamination. In still other cases, imaging systems are placed outside of a sterile field. However, the user then may have to twist and strain just to see an image and an additional person may be required to operate the imaging system.

Additionally, in a sterile environment such as an operating room (OR), it may be desirable to use an imaging system that is relatively small in size, portable, simple to use and easily cleanable. For example, in the OR it may be desirable to use an ultrasound imaging system having a relatively small footprint to visualize non-invasive surgical procedures. Also, if a clinician other than an ultrasonographer is using the ultrasound imaging system, simplicity of the imaging system is important for ease of use. Moreover, working in a sterile field, every crack and seam is a breeding ground of infectious bacteria. Hence, it may be desirable that the ultrasound imaging system be easily cleanable.

It may therefore be desirable to develop a design of a portable imaging system that may be configured to facilitate easy and quick cleaning and disinfecting and a method for cleaning and disinfecting a portable imaging system. More particularly there exists a need for a portable imaging system having a relatively small size and simple to use that may be wipeable and easily cleaned, thus allowing use of the imaging system in sterile environments.

BRIEF DESCRIPTION

In accordance with aspects of the present technique, a portable imaging system is presented. The system includes at least a display panel. Further, the system includes a control panel, where the display panel and the control panel include a seamless form factor of a single unit box, and where the seamless form factor is configured to aid in cleaning the system.

In accordance with further aspects of the present technique, a method of making a portable imaging system is presented. The method includes providing at least a display panel and a control panel, where the display panel and the control panel include a seamless form factor of a single unit box, and where the seamless form factor is configured to aid in cleaning the system.

In accordance with another aspect of the present technique, a method of cleaning a portable imaging system is presented, where the portable imaging system includes a display panel and a control panel, where the display panel and the control panel include a seamless form factor of a single unit box, and where the seamless form factor is configured to aid in cleaning the system. The method includes disinfecting the system by cleaning the system with a cleaning agent.

In accordance with yet another aspect of the present technique, a method of operating and cleaning a portable imaging system is presented, where the portable imaging system includes a display panel, and a control panel, where the display panel and the control panel include a seamless form factor of a single unit box, and where the seamless form factor is configured to aid in cleaning the system. The method includes using one or more buttons on the control panel, a stylus, or both, to operate the system. In addition, the method includes disinfecting the system by cleaning the system with a cleaning agent before operating the system, after operating the system, or both.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Although the exemplary embodiments illustrated hereinafter are described in the context of a medical imaging system, it will be appreciated that use of the diagnostic system in industrial applications are also contemplated in conjunction with the present technique. For example, the diagnostic system may find applications in industrial systems such as industrial imaging systems and non-destructive evaluation and inspection systems, such as pipeline inspection systems and liquid reactor inspection systems.

Figure 1:
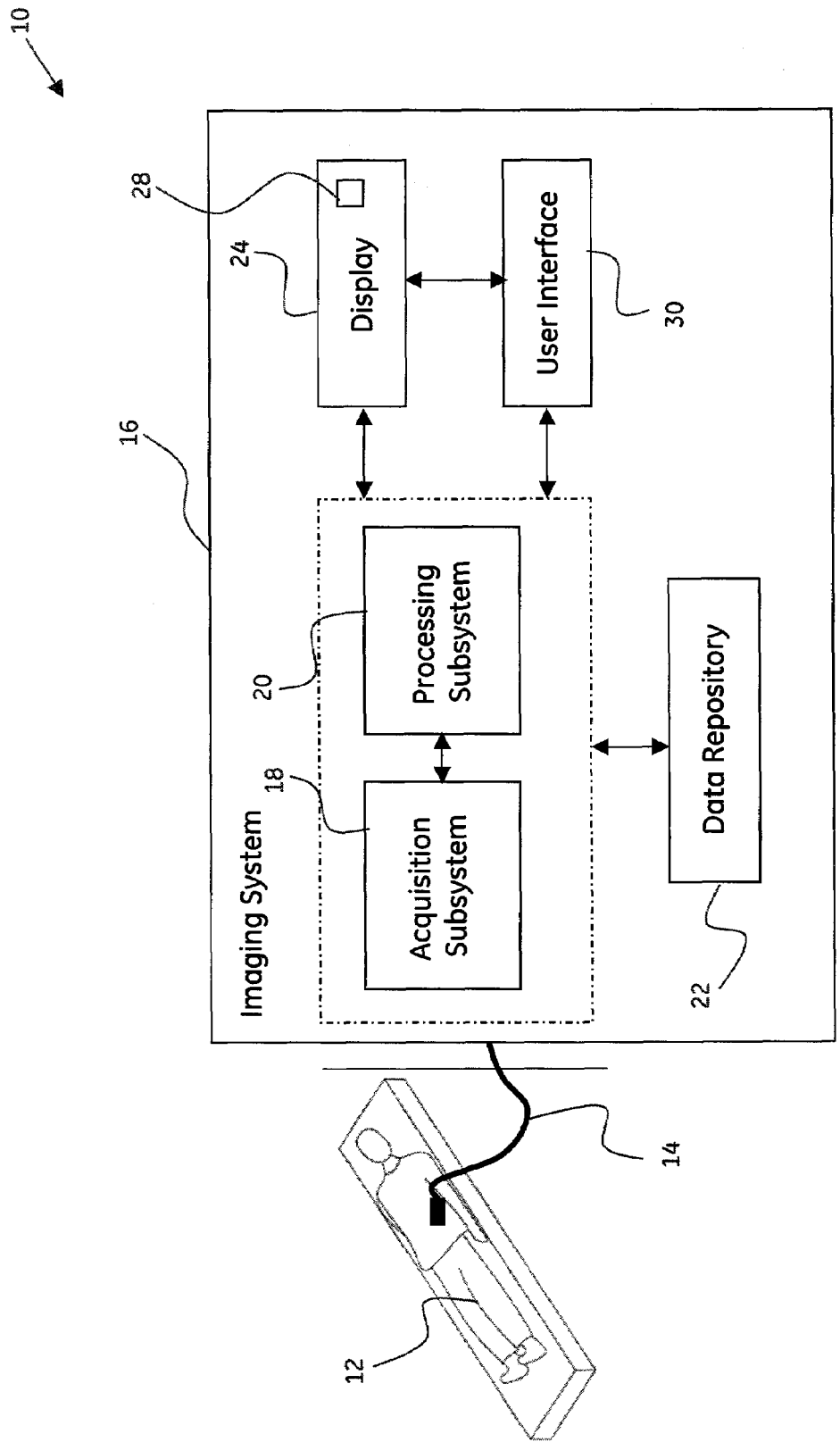
FIG. 1 is a block diagram of an exemplary diagnostic system, in accordance with aspects of the present technique.

FIG. 1 is a block diagram of an exemplary system 10 for use in diagnostic imaging in accordance with aspects of the present technique. The system 10 may be configured to acquire image data from a patient 12 via an image acquisition device 14. In one embodiment, the image acquisition device 14 may include a probe, where the probe may include an invasive probe, or a non-invasive or external probe, such as an external ultrasound probe, that is configured to aid in the acquisition of image data. By way of example, the image acquisition device 14 may include a probe, where the probe includes an imaging catheter, an endoscope, a laparoscope, a surgical probe, an external probe, or a probe adapted for interventional procedures. The image acquisition device 14 may also include a probe configured to facilitate acquisition of an image volume. It may be noted that the terms probe and image acquisition device may be used interchangeably.

Although the present example illustrates the image acquisition device 14 as being coupled to an imaging system via a probe cable, it will be understood that the probe may be coupled with the imaging system via other means, such as wireless means, for example. Also, in certain other embodiments, image data may be acquired via one or more sensors (not shown) that may be disposed on the patient 12. By way of example, the sensors may include physiological sensors (not shown), such as electrocardiogram (ECG) sensors and/or positional sensors, such as electromagnetic field sensors or inertial sensors. These sensors may be operationally coupled to a data acquisition device, such as an imaging system, via leads (not shown), for example.

The system 10 may also include a medical imaging system 16 that is in operative association with the image acquisition device 14. It should be noted that although the exemplary embodiments illustrated hereinafter are described in the context of a medical imaging system, other imaging systems and applications, such as industrial imaging systems and non-destructive evaluation and inspection systems, such as pipeline inspection systems and liquid reactor inspection systems, are also contemplated. Additionally, the exemplary embodiments illustrated and described hereinafter may find application in multi-modality imaging systems that employ ultrasound imaging in conjunction with other imaging modalities, position-tracking systems or other sensor systems. It may be noted that the other imaging modalities may include medical imaging systems, such as, but not limited to, an ultrasound imaging system, a computed tomography (CT) imaging system, a magnetic resonance (MR) imaging system, a nuclear imaging system, a positron emission topography system or an X-ray imaging system.

In a presently contemplated configuration, the medical imaging system 16 may include an acquisition subsystem 18 and a processing subsystem 20. Further, the acquisition subsystem 18 of the medical imaging system 16 may be configured to acquire image data representative of one or more anatomical regions of interest in the patient 12 via the image acquisition device 14. The image data acquired from the patient 12 may then be processed by the processing subsystem 20.

Additionally, the image data acquired and/or processed by the medical imaging system 16 may be employed to aid a clinician in identifying disease states, assessing need for treatment, determining suitable treatment options, and/or monitoring the effect of treatment on the disease states. In certain embodiments, the processing subsystem 20 may be further coupled to a storage system, such as a data repository 22, where the data repository 22 may be configured to receive and/or store image data.

Further, as illustrated in FIG. 1, the medical imaging system 16 may include a display 24 and a user interface 30. However, in certain embodiments, such as in a touch screen, the display 24 and the user interface 30 may overlap. Also, in some embodiments, the display 24 and the user interface 30 may include a common area. In accordance with aspects of the present technique, the display 24 of the medical imaging system 16 may be configured to display one or more images generated by the medical imaging system 16 based on the image data acquired via the image acquisition device 14. In accordance with exemplary aspects of the present technique, the display 24 may be configured to include display panel. Also, the display panel 24 may be configured to display an image representative of an anatomical region of interest of the patient 12, for example.

In addition, the user interface 30 of the medical imaging system 16 may include a human interface device (not shown) configured to facilitate the clinician in the acquisition of image data representative of the patient 12. The human interface device may include a mouse-type device, a trackball, a joystick, a stylus, or buttons configured to aid the clinician in acquiring image data representative of one or more regions of interest in the patient 12. However, as will be appreciated, other human interface devices, such as, but not limited to, a touch screen, may also be employed. Furthermore, in accordance with aspects of the present technique, the user interface 30 may be configured to aid the clinician in navigating through the images acquired by the medical imaging system 16. Additionally, the user interface 30 may also be configured to aid in manipulating and/or organizing the acquired image data for display on the display 24.

According to further aspects of the present technique, the imaging system 16 may also be configured to automatically adjust a brightness of the display panel 24 based on current ambient conditions. For example, if the ambient condition includes a substantially bright environment, then the imaging system 16 may be configured to enhance the brightness of the display panel 24. However, if the ambient condition includes a substantially dark environment, then the imaging system 16 may be configured to accordingly dim the brightness of the display panel 24. In a presently contemplated configuration, the imaging system 16 may be configured to automatically adjust the brightness of the display panel 24 via use of an ambient light sensor 28. It may be noted that although the ambient light sensor 28 is disposed in the display area 24 in the embodiment illustrated in FIG. 1, it may be appreciated that the ambient light sensor 28 may be disposed at other locations on the imaging system 16.

In accordance with exemplary aspects of the present technique, the imaging system 16 may be configured to have a seamless form factor of a single unit box. By implementing the imaging system 16 having a seamless form factor advantageously enables a user, such as a clinician, to quickly and easily clean and disinfect the imaging system 16, thereby reducing any risk of contamination and hence enhancing patient care.

Figure 2:
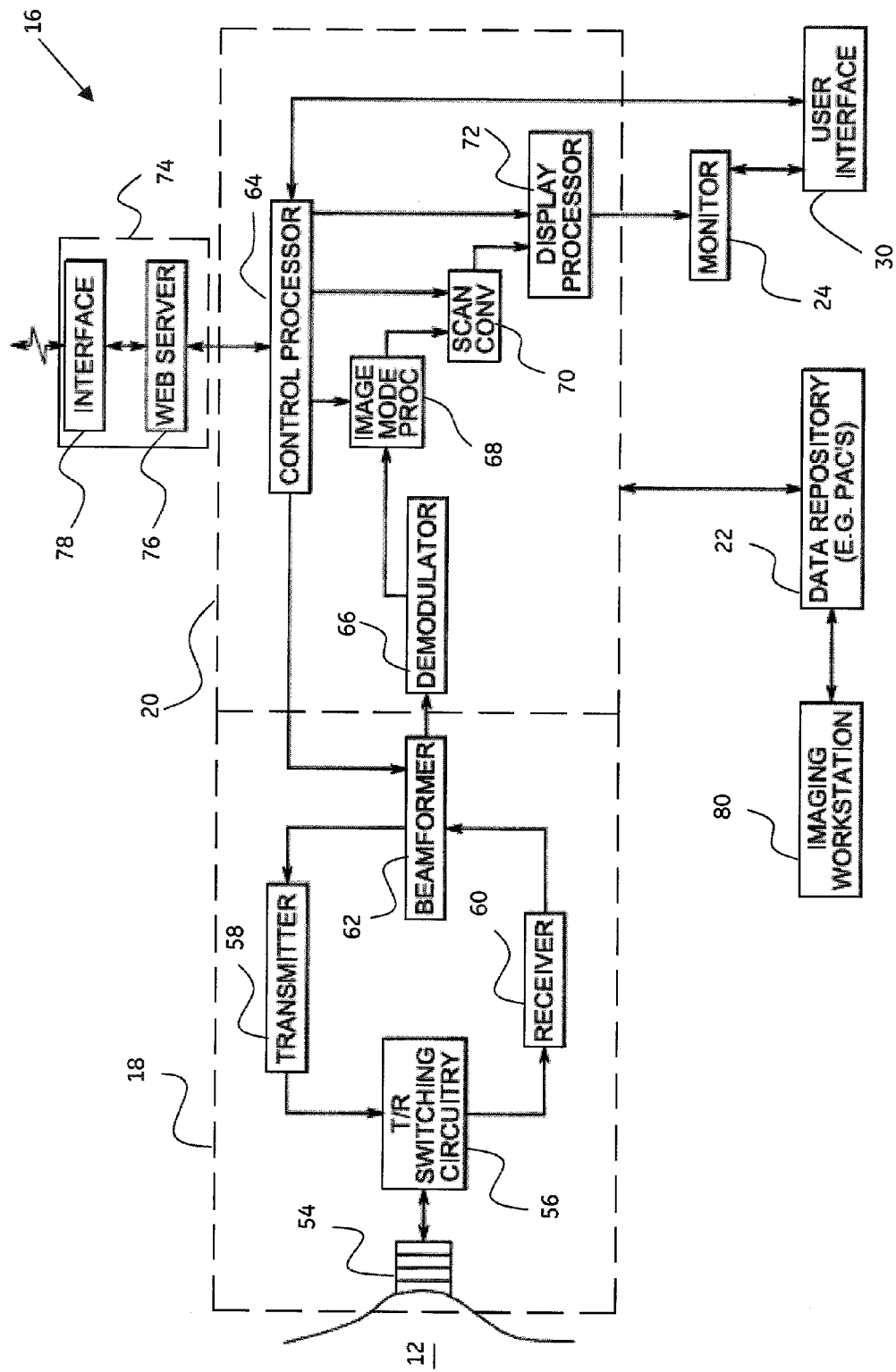
FIG. 2 is a block diagram of an exemplary imaging system in the form of an ultrasound imaging system for use in the exemplary diagnostic system of FIG. 1.

As previously noted, the medical imaging system 16 may include an ultrasound imaging system. FIG. 2 is a block diagram of an embodiment of the medical imaging system 16 of FIG. 1, where the medical imaging system 16 is shown as including an ultrasound imaging system 16. Furthermore, the ultrasound imaging system 16 is shown as including the acquisition subsystem 18 and the processing subsystem 20, as previously described. The acquisition subsystem 18 may include a transducer assembly 54. In addition, the acquisition subsystem 18 includes transmit/receive (T/R) switching circuitry 56, a transmitter 58, a receiver 60, and a beamformer 62. In one embodiment, the transducer assembly 54 may be disposed in the image acquisition device 14 (see FIG. 1). Also, in certain embodiments, the transducer assembly 54 may include a plurality of transducer elements (not shown) arranged in a spaced relationship to form a transducer array, such as a one-dimensional or two-dimensional transducer array, for example. Additionally, the transducer assembly 54 may include an interconnect structure (not shown) configured to facilitate operatively coupling the transducer array to an external device (not shown), such as, but not limited to, a cable assembly or associated electronics. The interconnect structure may be configured to couple the transducer array to the T/R switching circuitry 56.

The processing subsystem 20 includes a control processor 64, a demodulator 66, an imaging mode processor 68, a scan converter 70 and a display processor 72. The display processor 72 is further coupled to a display monitor, such as the display panel 24 (see FIG. 1), for displaying images. User interface, such as the user interface 30 (see FIG. 1), interacts with the control processor 64 and the display 24. The control processor 64 may also be coupled to a remote connectivity subsystem 74 including a web server 76 and a remote connectivity interface 78. The processing subsystem 20 may be further coupled to the data repository 22 (see FIG. 1) configured to receive ultrasound image data, as previously noted with reference to FIG. 1. The data repository 22 interacts with an imaging workstation 80.

The aforementioned components may be dedicated hardware elements such as circuit boards with digital signal processors or may be software running on a general purpose computer or processor such as a commercial, off-the-shelf personal computer (PC). The various components may be combined or separated according to various embodiments of the present technique. Thus, those skilled in the art will appreciate that the present ultrasound imaging system 16 is provided by way of example, and the present techniques are in no way limited by the specific system configuration.

In the acquisition subsystem 18, the transducer assembly 54 is acoustically coupled to the patient 12 (see FIG. 1), either by direct contact with the patient 12 or by coupling via an acoustic gel. The transducer assembly 54 is coupled to the transmit/receive (T/R) switching circuitry 56. Also, the T/R switching circuitry 56 is in operative association with an output of the transmitter 58 and an input of the receiver 60. The output of the receiver 60 is an input to the beamformer 62. In addition, the beamformer 62 is further coupled to an input of the transmitter 58 and to an input of the demodulator 66. The beamformer 62 is also operatively coupled to the control processor 64 as shown in FIG. 2.

In the processing subsystem 20, the output of demodulator 66 is in operative association with an input of the imaging mode processor 68. Additionally, the control processor 64 interfaces with the imaging mode processor 68, the scan converter 70 and the display processor 72. An output of the imaging mode processor 68 is coupled to an input of the scan converter 70. Also, an output of the scan converter 70 is operatively coupled to an input of the display processor 72. The output of the display processor 72 is coupled to the display 24.

The ultrasound imaging system 16 transmits ultrasound energy into the patient 12 and receives and processes backscattered ultrasound signals from the patient 12 to create and display an image. To generate a transmitted beam of ultrasound energy, the control processor 64 sends command data to the beamformer 62 to generate transmit parameters to create a beam of a desired shape originating from a certain point at the surface of the transducer assembly 54 at a desired steering angle. The transmit parameters are sent from the beamformer 62 to the transmitter 58. The transmitter 58 uses the transmit parameters to properly encode transmit signals to be sent to the transducer assembly 54 through the T/R switching circuitry 56. The transmit signals are set at certain levels and phases with respect to each other and are provided to individual transducer elements of the transducer assembly 54. The transmit signals excite the transducer elements to emit ultrasound waves with the same phase and level relationships. As a result, a transmitted beam of ultrasound energy is formed in the patient 12 along a scan line when the transducer assembly 54 is acoustically coupled to the patient 12 by using, for example, ultrasound gel. The process is known as electronic scanning.

In one embodiment, the transducer assembly 54 may be a two-way transducer. When ultrasound waves are transmitted into a patient 12, the ultrasound waves are backscattered off the tissue and blood samples within the patient 12. The transducer assembly 54 receives the backscattered waves at different times, depending on the distance into the tissue they return from and the angle with respect to the surface of the transducer assembly 54 at which they return. The transducer elements convert the ultrasound energy from the backscattered waves into electrical signals.

The electrical signals are then routed through the T/R switching circuitry 56 to the receiver 60. The receiver 60 amplifies and digitizes the received signals and provides other functions such as gain compensation. The digitized received signals corresponding to the backscattered waves received by each transducer element at various times preserve the amplitude and phase information of the backscattered waves.

The digitized signals are sent to the beamformer 62. The control processor 64 sends command data to beamformer 62. The beamformer 62 uses the command data to form a receive beam originating from a point on the surface of the transducer assembly 54 at a steering angle typically corresponding to the point and steering angle of the previous ultrasound beam transmitted along a scan line. The beamformer 62 operates on the appropriate received signals by performing time delaying and focusing, according to the instructions of the command data from the control processor 64, to create received beam signals corresponding to sample volumes along a scan line within the patient 12. The phase, amplitude, and timing information of the received signals from the various transducer elements are used to create the received beam signals.

The received beam signals are sent to the processing subsystem 20. The demodulator 66 demodulates the received beam signals to create pairs of I and Q demodulated data values corresponding to sample volumes along the scan line. Demodulation is accomplished by comparing the phase and amplitude of the received beam signals to a reference frequency. The I and Q demodulated data values preserve the phase and amplitude information of the received signals.

The demodulated data is transferred to the imaging mode processor 68. The imaging mode processor 68 uses parameter estimation techniques to generate imaging parameter values from the demodulated data in scan sequence format. The imaging parameters may include parameters corresponding to various possible imaging modes such as B-mode, color velocity mode, spectral Doppler mode, and tissue velocity imaging mode, for example. The imaging parameter values are passed to the scan converter 70. The scan converter 70 processes the parameter data by performing a translation from scan sequence format to display format. The translation includes performing interpolation operations on the parameter data to create display pixel data in the display format.

The scan converted pixel data is sent to the display processor 72 to perform any final spatial or temporal filtering of the scan converted pixel data, to apply grayscale or color to the scan converted pixel data, and to convert the digital pixel data to analog data for display on the display 24. The user interface 30 is coupled to the control processor 64 to allow a user to interface with the ultrasound imaging system 16 based on the data displayed on the display 24.

Figure 3:
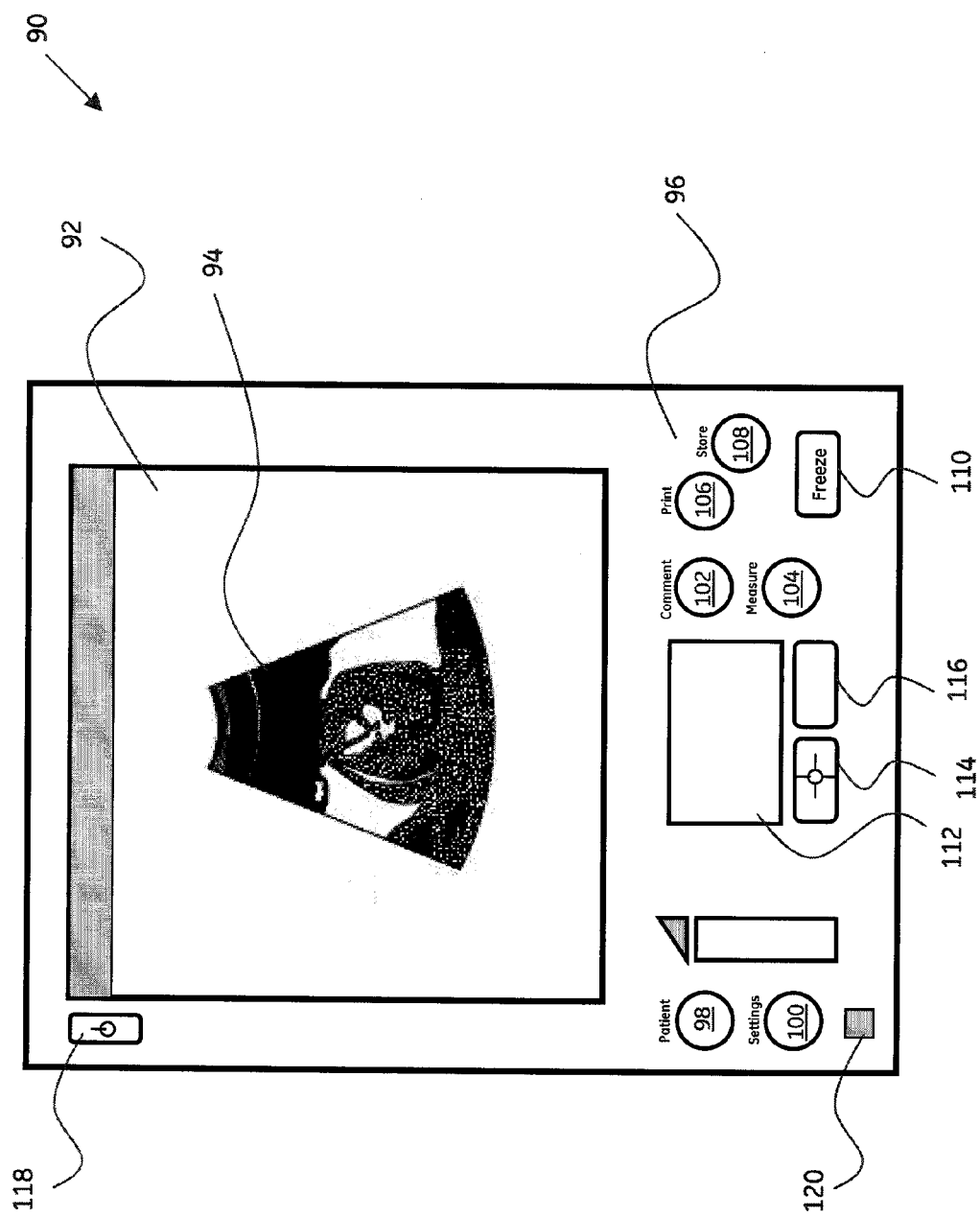
FIG. 3 is a diagrammatic illustration of an exemplary portable imaging system, in accordance with aspects of the present technique.

FIG. 3 illustrates an exemplary portable imaging system 90. In the present example, the portable imaging system 90 may include an ultrasound imaging system, such as the ultrasound imaging system 16 (see FIG. 2). The imaging system 90 may include a hand held imaging system or a hand carried imaging system. Furthermore, the imaging system 90 may include a monolith design. In other words, the imaging system 90 may include a single piece unit. Additionally, the imaging system 90 may be configured to be operationally coupled to a small footprint cart, a pole stand, or a stretcher. Alternatively, the imaging system 90 may be wall mounted.

Further, the imaging system 90 may include a display panel 92. This display panel 92 may include a display panel such as the display panel 24 (see FIG. 1). The display panel 92 may be configured to facilitate display of an image 94, where the image 94 may be representative of a region of interest in a patient, such as the patient 12 (see FIG. 1), for example.

In accordance with further aspects of the present technique, the imaging system 90 may also include a control panel 96. It may be noted that the control panel 96 may include a user interface such as the user interface 30 (see FIG. 1). Also the control panel 96 may include one or more buttons, where the buttons may be configured to aid in the imaging of the patient 12 (see FIG. 1). In certain embodiments, the control panel 96 may be configured to include buttons that may be configured to perform commonly used functions of the imaging system 90. The commonly performed functions may include a Freeze function, a Print function, a Store function, or a Comment function, to name a few. In a presently contemplated configuration, the buttons in the control panel 96 of the imaging system 90 may include hard buttons. In accordance with aspects of the present technique, the buttons may include membrane covered buttons. These membrane covered buttons may be configured to provide a substantially impervious enclosure to the buttons, thereby protecting the buttons from fluid splatter and/or chemical cleaning agents. In addition, the membrane covered buttons facilitates easy cleaning and disinfecting by quickly and easily wiping surfaces of the buttons after each use of the imaging system 90.

As noted hereinabove, commonly used functions may be available via the membrane covered buttons in the control panel 96 of the imaging system 90. It may be noted that the hard keys located in control panel 96 may be representative of keys used to control features outside of a typical scanning operation. Examples of commonly performed functions may include a Print function, a Comment (annotate) function, a Settings function, a Store function, and a Freeze function, as previously noted.

In the example illustrated in FIG. 3, the commonly performed functions may be performed via use of buttons such as a Patient button 98, a Settings button 100, a Comment button 102, a Measure button 104, a Print button 106, a Store button 108, and a Freeze button 110, for example. A clinician may enter patient data using the Patient button 98, while the clinician may take measurements of the image 94 via use of the Measure button 104. Reference numeral 112 may be representative of a mouse pad. Further, reference numeral 114 may be representative of a left click button on the mouse pad 112, where the left click button 114 may be used for setting a cursor, setting a measuring caliper, or clicking on a menu item, for example. Similarly, a right click button on the mouse pad 112 may generally be represented by reference numeral 116, where the right click button 116 may be employed to aid in toggling the cursor on the display panel 92 between an ON state and an OFF state. In addition, a Power button may generally be represented by reference numeral 118.

By implementing the control panel 96 as described hereinabove, the membrane covered buttons may be separated from the other controls and located in the control panel 96. By locating these membrane covered buttons in the control panel 96, the membrane covered buttons are available at all times. For example, a Freeze function and a Store function may be applied at any time, independent of a current mode of operation of the imaging system 90, such as a color mode, a Doppler mode, or a B-mode of operation of the imaging system. Also, the commonly used functions, like Freeze, Store, and Depth, may be controlled via use of the membrane covered hard keys. The design of the hard keys allow for tactile feedback, like raised textures and back lighting for good ergonomics and ease of use.

In accordance with further aspects of the present technique, the display panel 92 and the control panel 96 may be arranged such that the imaging system 90 includes a seamless form factor of a single unit box. In other words, the display panel 92 and the control panel 96 including the hard buttons may have a seamless facade, thereby allowing the console and the screen to be wiped clean with disinfectant and hence prevent places for bacteria to accumulate in hard to clean cracks. Additionally, the seamless design of the facade of the imaging system 90 allows internal components of the imaging system 90 to be protected from fluid splatter. For example, the membrane covered buttons may be impervious to any fluid splatter and these buttons may be easily wiped and cleaned.

Moreover, in certain embodiments, the imaging system 90 may have a height in a range from about 250 mm to about 300 mm. Also, the imaging system 90 may have a width in a range from about 250 mm to about 300 mm. In addition, the imaging system 90 may have a depth in a range from about 30 mm to about 50 mm. Furthermore, the imaging system 90 may have a weight in a range from about 2 kilograms to about 4 kilograms.

In accordance with further aspects of the present technique, the imaging system 90 may be configured to automatically adjust a brightness of the display panel 92 based on current ambient conditions. For example, if the ambient condition includes a substantially bright environment, then the imaging system 90 may be configured to enhance the brightness of the display panel 92. However, if the ambient condition includes a substantially dark environment, then the imaging system 90 may be configured to accordingly dim the brightness of the display panel 92. In a presently contemplated configuration, the imaging system 90 may include an ambient light sensor 120, where the ambient light sensor 120 may be configured to aid the imaging system 90 in sensing current ambient conditions and automatically adjusting the brightness of the display panel 92. Also, in the present example, the ambient light sensor 120 is shown as being located in the control panel 96. However, the ambient light sensor 120 may also be located else where on the imaging system 90.

Figure 4:
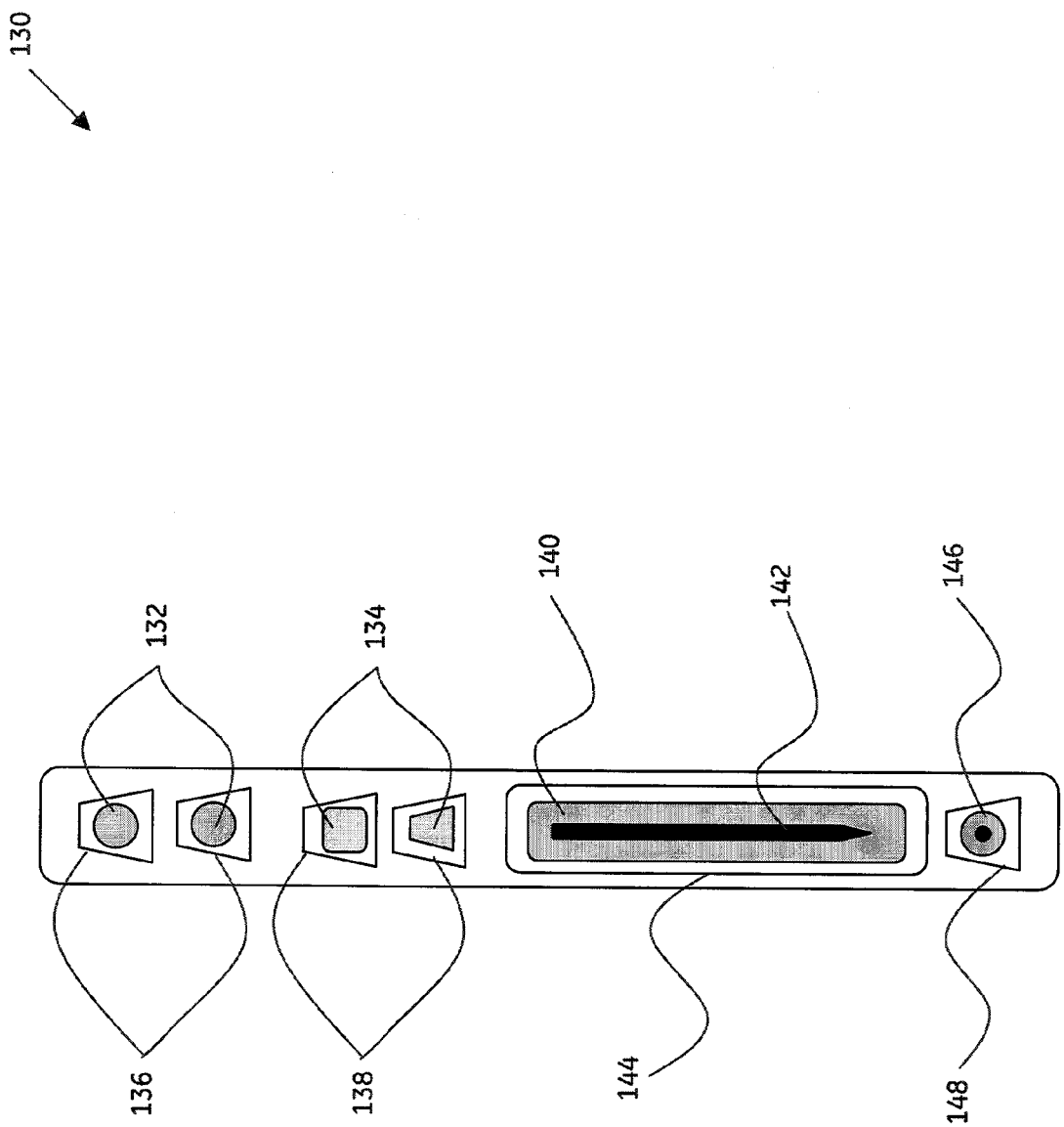
FIG. 4 is a diagrammatic illustration of a side view of the exemplary portable imaging system of FIG. 3, in accordance with aspects of the present technique.

Furthermore, the imaging system 90 may also include one or more ports, one or more connectors, or both. Referring now to FIG. 4, a diagrammatical illustration of a side view 130 of the imaging system 90 (see FIG. 3) is depicted. Reference numeral 132 may be representative of the one or more ports, while the one or more connectors may generally be represented by reference numeral 134. It may be noted that the one or more ports 132, the one or more connectors 134, or both, may be configured to allow one or more devices to be operationally coupled to the imaging system 90. For example, one or more image acquisition devices, such as, but not limited to, probes, may be coupled to the imaging system 90 via the one or more ports 132 and/or the one or more connectors 134. In addition, the imaging system 90 may also include one or more protective flaps, where the flaps may be configured to cover the ports 132 and/or the connectors 134. In the example depicted in FIG. 4, reference numeral 136 may be representative of the protective flaps configured to cover the ports 132, while the protective flaps configured to cover the connectors 134 may generally be represented by reference numeral 138.

In accordance with aspects of the present technique, the imaging system 90 may be recharged via a freestanding dock, a wall-mounted charging dock, a portable charger adapter, or a combination thereof. Referring again to the embodiment illustrated in FIG. 4, reference numeral 146 may be representative of a charging connector, while a protective flap configured to cover the charging connector may generally be represented by reference numeral 148. The imaging system 90 may also be configured to include a storage area 140 for a touch stylus 142. Reference numeral 144 may generally be representative of a protective flap configured to cover the storage area 140 and/or the stylus 142. It may be noted that these protective flaps 136, 138, 144, 148 may include rubber flaps or silicone flaps, for example.

By providing the protective flaps 136, 138, 144, 148, the ports 132, the connectors 134, 146, and/or the stylus 142 may be protected from fluid splatter and/or contamination. Additionally, the protective flaps 136, 138, 144, 148 may be configured to allow the clinician to easily wipe and clean the imaging system 90.

With returning reference to FIG. 3, a battery (not shown in FIG. 3) in the imaging system 90 may have a life of about one hour. Furthermore, the imaging system 90 may be designed to include a robust unit. For example, the imaging system 90 may be configured to be droppable from a height of about 80 cm, in certain embodiments. Additionally, the imaging system 90 may be configured to boot up in a time of less than about 10 seconds.

By implementing the imaging system as described hereinabove, a portable, simple to use imaging system may be produced, where the imaging system has a seamless facade. This design advantageously allows the imaging system to be easily cleaned and hence allow use of the imaging systems in sterile environments.

Figure 5:
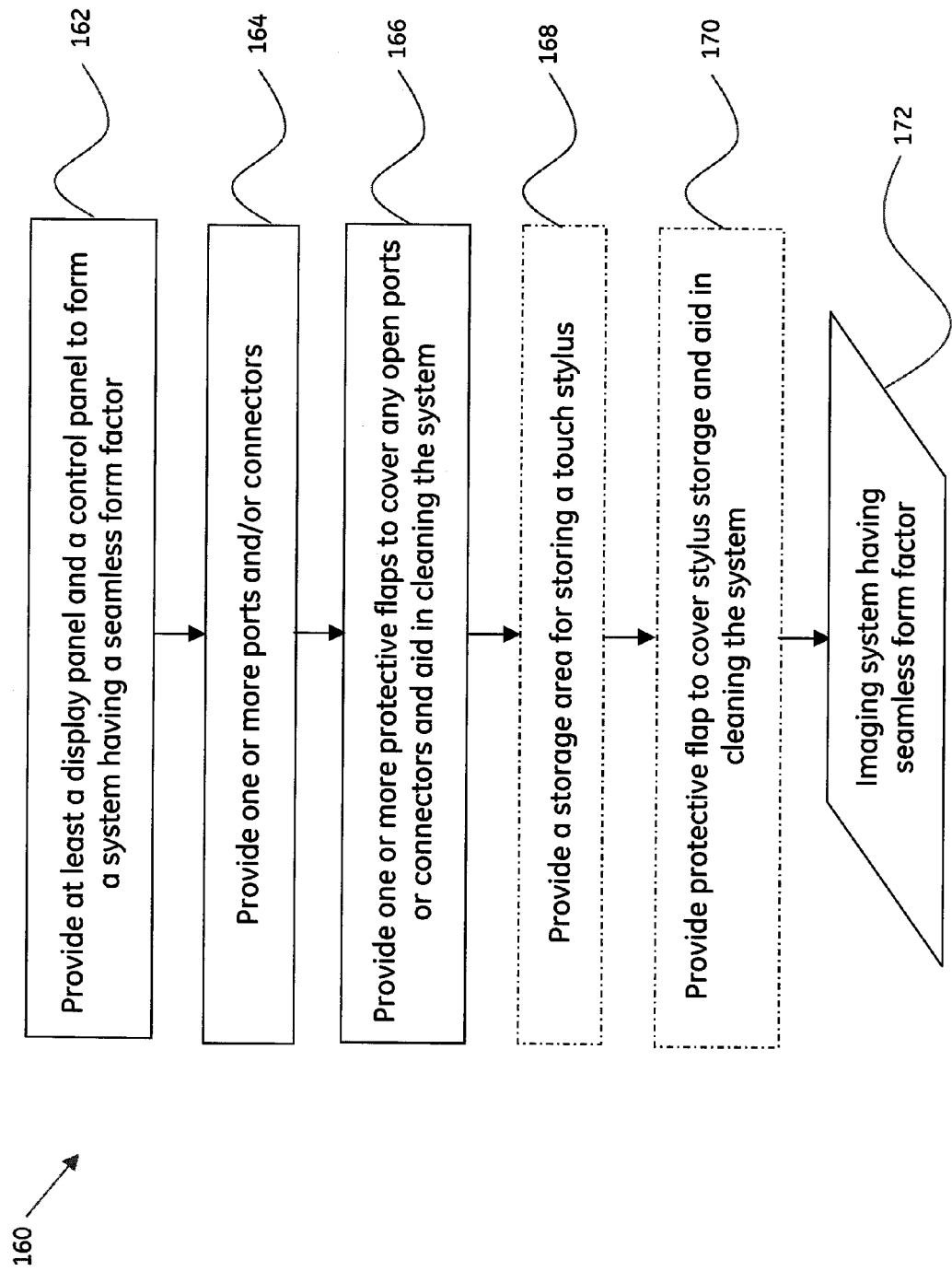
FIG. 5 is a flow chart illustrating a process of making the exemplary portable imaging system of FIG. 3, in accordance with aspects of the present technique.

In accordance with further aspects of the present technique, a method of making the exemplary imaging system 90 of FIG. 3 is presented. Turning now to FIG. 5, a flow chart 160 illustrating the exemplary method of making the exemplary portable imaging system 90 is depicted. The method starts at step 162, where at least a display panel, such as the display panel 92 (see FIG. 3) may be provided. This display panel may be configured to display an image, such as the image 94 (see FIG. 3). For example, an image representative of one or more regions of interest of the patient 12 (see FIG. 1) may be displayed on the display panel 92.

With continuing reference to step 162, a control panel may be provided. More particularly, the display panel and the control panel may be provided to form an exemplary imaging system, where the display panel and the control panel may be configured to have a seamless form factor of a single unit box. This imaging system having the seamless form factor advantageously aids in cleaning and disinfecting the imaging system. In other words, the imaging system having the seamless form factor may be configured to aid in enhancing ease of cleaning and disinfecting the imaging system. By way of example, the seamless design of the imaging system circumvents need for any seams and/or lines where the components join together, thereby reducing the risk of contamination by infectious diseases and/or bacteria in a medical environment in which the imaging system may be used.

Further, the control panel may be configured to include one or more buttons, where the buttons may be configured to aid in performing commonly used functions. In certain embodiments, the commonly used functions may include functions, such as, but not limited to, a Print function, a Store function, a Freeze function, or the like. Also, these buttons on the control panel may be configured to include membrane covered keys. Here again, by providing the one or more membrane covered keys as described hereinabove, a similar risk of contamination that is generally posed around mechanical buttons, keypads, and/or trackballs may be circumvented.

Additionally, at step 164, one or more ports may be provided, where the one or more ports may be configured to facilitate operatively coupling components such as probes to the imaging system. Moreover, at step 166, one or more protective flaps may be provided, where the flaps may be configured to cover any open ports and/or connectors, thereby protecting the ports and/or connectors from fluid splatter. In addition, by providing the one or more protective flaps to cover any open ports, ease of cleaning and disinfecting the imaging system may be greatly enhanced, thereby reducing any risk of contamination.

Furthermore, at step 168, a storage area for a touch stylus may be provided. Moreover, at step 170, a protective flap configured to cover the storage area for the touch styles may be provided, thereby protecting the storage area from fluid splatter. Here again, by providing the protective flap to cover the stylus storage area, ease of cleaning and disinfecting the imaging system may be greatly enhanced, thereby reducing any risk of contamination. Subsequent to steps 162-170, an imaging system having a seamless form factor that advantageously aids in cleaning the imaging system may be formed. This imaging system having the seamless form factor may generally be represented by reference numeral 172.

Figure 6:
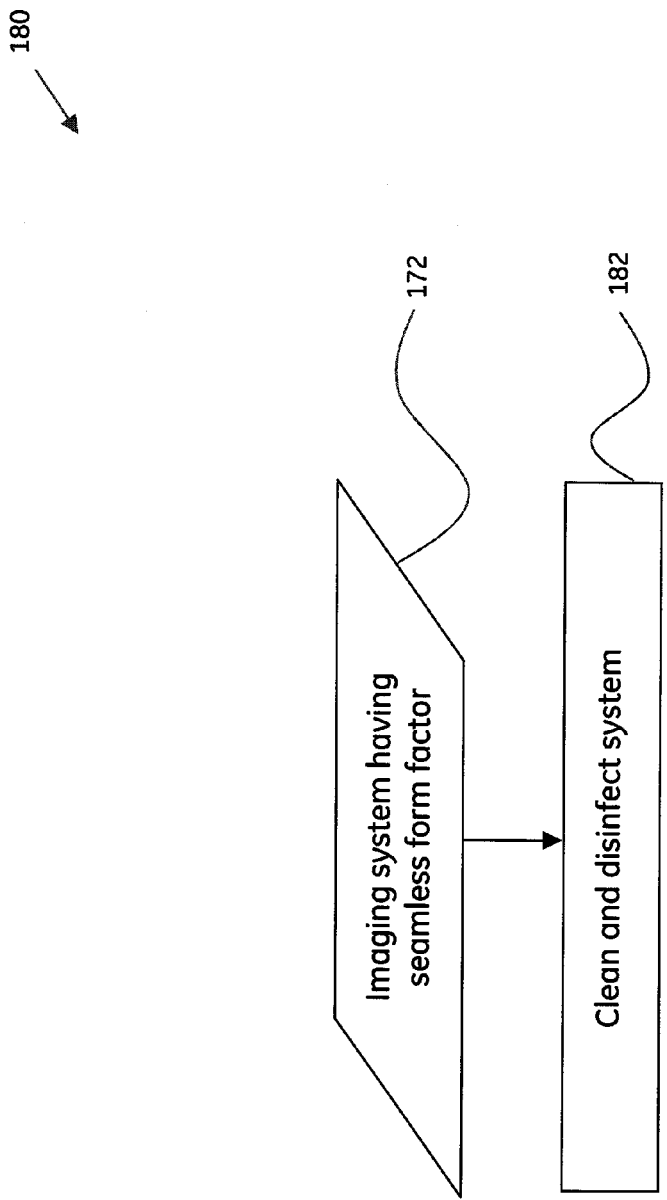
FIG. 6 is a flow chart illustrating a process of cleaning the exemplary portable imaging system of FIG. 3, in accordance with aspects of the present technique.

In accordance with further aspects of the present technique, a method of cleaning the exemplary imaging system 90 of FIG. 3 is presented. Turning now to FIG. 6, a flow chart 180 illustrating the exemplary method of cleaning the portable imaging system 90 is depicted. As previously described, the imaging system 90 may include a display panel 92 (see FIG. 3) and a control panel 96, where the display panel and the control panel may be configured to have a seamless form factor of a single unit box. Further, the control panel may include one or more buttons configured to aid in performing commonly used functions like Print, Freeze, Store, or Comment. In accordance with aspects of the present technique, the buttons may include membrane covered buttons. These membrane covered buttons may be configured to provide a substantially impervious enclosure to the buttons by protecting the buttons from fluid splatter and/or chemical cleaning agents and allowing the buttons to be disinfected by quickly and easily wiping surfaces of the buttons after each use of the imaging system 172.

As previously described, the imaging system 172 having the seamless form factor advantageously aids in cleaning and disinfecting the imaging system 172. In other words, the imaging system having the seamless form factor may be configured to aid in enhancing ease of cleaning and disinfecting the imaging system 172 as the seamless design of the imaging system 172 circumvents need for any seams and/or lines where the components join together, thereby reducing the risk of contamination by infectious diseases and/or bacteria in a medical environment in which the imaging system 172 may be used. In certain embodiments, during an imaging session using the imaging system 172, dirt, bacteria, viruses, other liquids, or combinations thereof, may be splashed onto the imaging system 172, thereby calling for a thorough cleaning and disinfecting of the imaging system 172 before the imaging system 172 may be reused. Accordingly, at step 182, the imaging system 172 may be wiped clean. A medical grade cleaning agent may be used to clean and disinfect the imaging system 172. For example, the cleaning agent may include isopropyl alcohol, quarternary ammonium, phenol, ammonium chlorides, hydrogen peroxide, ethyl alcohol, diluted bleach, or other medical grade antifungal, antibacterial and antiviral disinfecting agents. The seamless form factor of the imaging system 172 advantageously provides a relatively smooth surface, thereby allowing the clinician to quickly and easily clean and disinfect the imaging system 172.

Figure 7:
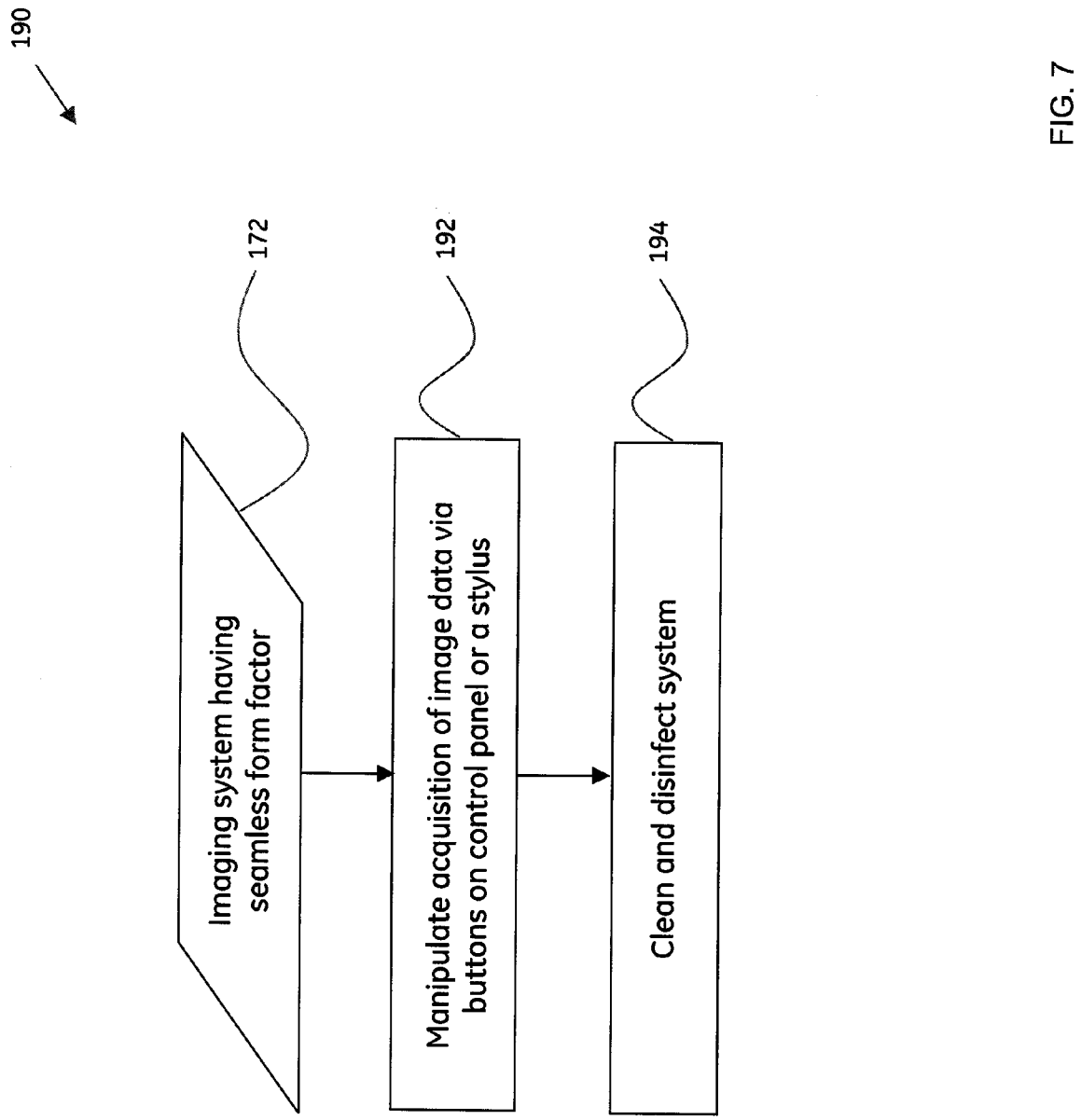
FIG. 7 is a flow chart illustrating a process of operating and cleaning the exemplary portable imaging system of FIG. 3, in accordance with aspects of the present technique.

In accordance with further aspects of the present technique, a method of operating and cleaning the exemplary imaging system 90 of FIG. 3 is presented. Turning now to FIG. 7, a flow chart 190 illustrating the exemplary method of operating and cleaning the portable imaging system 90 is depicted. As previously described, the imaging system 90 (see FIG. 5) may include a display panel 92 (see FIG. 3), where the display panel 92 may be configured to display an image, such as the image 94 (see FIG. 3), where the image 94 may be representative of an anatomical region of interest of the patient 12 (see FIG. 1). In addition, the imaging system 90 may also include the control panel 96 (see FIG. 3). More particularly, the display panel and the control panel may be provided to form an exemplary imaging system, where the display panel and the control panel may be configured to have a seamless form factor of a single unit box. This imaging system having the seamless form factor advantageously aids in cleaning and disinfecting the imaging system.

The method starts at step 192, where an image representative of one or more regions of interest in the patient 12 (see FIG. 1) may be displayed on the display panel of the imaging system 172. Image data representative of the one or more regions of interest may be obtained by the imaging system 172. In certain embodiments, the acquisition of the image data may be accomplished via use of one or more buttons on the control panel, where the one or more buttons may be configured to perform commonly used functions like Freeze, Store, Print, or Comment. Alternatively, a stylus may be used to aid in the acquisition of the image data at step 192.

Once an imaging session is concluded, it may be desirable to thoroughly clean the imaging system 172. According to aspects of the present technique, the imaging system 172 may be cleaned, as indicated by step 194. In one embodiment, cleaning agents such as, but not limited to, medical grade antibacterial and/or antiviral disinfecting agents may be used. More particularly, a clinician may use the disinfecting agents to wipe the seamless facade of the imaging system 172 quickly and easily, thereby enhancing clinical workflow and patient care.

The exemplary portable imaging system and the method for imaging using the exemplary portable imaging system described hereinabove dramatically enhance clinical workflow and patient care as the imaging system having the seamless form factor may be quickly and easily cleaned and disinfected. In other words, the seamless design of the console of the imaging system allows users to quickly wipe the imaging system with disinfectant, thereby saving time and allowing the imaging system to be used in exacting environments, such as sterile operating rooms. Additionally, the membrane covered hard keys allow the console to wiped clean with disinfectant and prevent places for bacteria to accumulate in hard to clean cracks. Also, the internal components of the system may be protected from fluid splatter.

In addition, the substantially small size of the imaging system allows the imaging system to fit into more tight, crowded rooms, like the operating room or an emergency crash room. The imaging system may also be attached to an intra-venous (IV) pole already in the room or to a small stand. Further, the imaging system may be hand carried from room to room as needed. Moreover, the imaging system may be placed into a wall mounted charging dock that is out of the way but readily available. Also, the imaging system may be fit into cramped areas like ambulances and helicopters.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:
1. A portable imaging system, comprising:
at least a display panel;
and a control panel, wherein the display panel and the control panel comprise a seamless form factor of a single unit box and wherein the seamless form factor provides a surface that prevents places for bacteria to accumulate.

2. The system of claim 1, wherein the display panel is configured to display an image representative of an anatomical region of interest in a patient.

3. The system of claim 1, wherein the control panel comprises one or more buttons configured to aid in performing imaging functions and cleaning the system.

4. The system of claim 1, wherein the system comprises a hand holdable or a hand carryable imaging system.

5. The system of claim 4, wherein the system comprises an ultrasound imaging system.

6. The system of claim 1, further comprising one or more ports, one or more connectors, or both, wherein the one or more ports, the one or more connectors, or both, are configured to facilitate operatively coupling one or more probes to the system.

7. The system of claim 6, further comprising one or more protective flaps configured to protect any ports or connectors from fluid splatter and aid in cleaning the system.

8. The system of claim 7, wherein the one or more protective flaps comprise rubber flaps, silicone flaps, or a combination thereof.

9. The system of claim 1, further comprising storage for a touch stylus.

10. The system of claim 9, further comprising a protective flap configured to protect the storage for the touch stylus from fluid splatter and aid in cleaning the system.

11. A method of making a portable imaging system, the method comprising:
providing at least a display panel and a control panel, wherein the display panel and the control panel comprise a seamless form factor of a single unit box, and wherein the seamless form factor provides a surface that prevents places for bacteria to accumulate.

12. The method of claim 11, further comprising providing one or more buttons on the control panel, wherein the one or more buttons comprise membrane covered buttons configured to aid in performing imaging functions and cleaning the system.

13. The method of claim 11, further comprising providing one or more ports, one or more connectors, or both, wherein the one or more ports, the one or more connectors, or both, are configured to facilitate operatively coupling one or more probes to the system.

14. The method of claim 13, further comprising providing one or more protective flaps configured to protect any ports or connectors from fluid splatter and aid in cleaning the system.

15. The method of claim 11, further comprising providing a storage for a touch stylus.

16. The method of claim 15, further comprising providing a protective flap configured to protect the storage for the touch stylus from fluid splatter and aid in cleaning the system.

17. A method of cleaning a portable imaging system, wherein the portable imaging system comprises:
a display panel;
a control panel, wherein the display panel and the control panel comprise a seamless form factor of a single unit box, and wherein the seamless form factor provides a surface that prevents places for bacteria to accumulate; and
the method comprising:
disinfecting the system by cleaning the system with a cleaning agent.

18. The method of claim 17, wherein the cleaning agent comprises isopropyl alcohol, quarternary ammonium, phenol, ammonium chlorides, hydrogen peroxide, ethyl alcohol, diluted bleach, other medical grade antifungal, antibacterial and antiviral disinfecting agents, or combinations thereof.

19. A method of operating and cleaning a portable imaging system, wherein the portable imaging system comprises:
a display panel;
a control panel,
wherein the display panel and the control panel comprise a seamless form factor of a single unit box, and wherein the seamless form factor provides a surface that prevents places for bacteria to accumulate;
the method comprising:
using one or more buttons on the control panel, a stylus, or both, to operate the system; and
disinfecting the system by cleaning the system with a cleaning agent before operating the system, after operating the system, or both.

20. The method of claim 19, wherein the cleaning agent comprises isopropyl alcohol, quarternary ammonium, phenol, ammonium chlorides, hydrogen peroxide, ethyl alcohol, diluted bleach, other medical grade antifungal, antibacterial and antiviral disinfecting agents, or combinations thereof.

21. The system of claim 1, wherein the control panel comprises one or more membrane covered buttons forming one or more substantially impervious button enclosures.

22. The system of claim 1, wherein the seamless form factor defines a smooth surface along the display panel and the control panel.

23. The system of claim 22, wherein the control panel comprises one or more membrane covered buttons, wherein the membrane covered buttons are hard buttons, the hard buttons defining a smooth surface along the control panel.

24. The system of claim 6, wherein one of the ports is configured to receive therein a connector of the one or more probes.

25. The system of claim 7, wherein the protective flaps are configured to cover the one or more ports or connectors and allow access thereto when not covered.

26. The system of claim 1, further comprising a processing subsystem configured to process medical image data of a patient acquired from an ultrasound probe coupled to the portable imaging system.

27. The system of claim 1, wherein the display panel comprises a touch screen.

28. The method of claim 11, wherein the display panel comprises a touch screen.

29. The method of claim 17, wherein the display panel comprises a touch screen.

30. The method of claim 19, wherein the display panel comprises a touch screen.

* * * * *